US005716927A

United States Patent [19]

Balschmidt et al.

[11] Patent Number: 5,716,927
[45] Date of Patent: *Feb. 10, 1998

[54] INSULIN ANALOGS HAVING A MODIFIED B-CHAIN

[75] Inventors: Per Balschmidt, Esperdaerde; Jens Jørgen Veilgaard Brange, Klampenborg, both of Denmark

[73] Assignee: Novo Nordisk A/S, Bagsvaerd, Denmark

[*] Notice: The term of this patent shall not extend beyond the expiration date of Pat. No. 5,164,364.

[21] Appl. No.: 531,842

[22] Filed: Sep. 21, 1995

Related U.S. Application Data

[63] Continuation of Ser. No. 275,196, Jul. 14, 1994, abandoned, which is a continuation of Ser. No. 976,805, Nov. 16, 1992, abandoned, which is a continuation-in-part of Ser. No. 453,445, Dec. 20, 1989, Pat. No. 5,164,366, which is a continuation-in-part of Ser. No. 416,218, Oct. 2, 1989, abandoned, and a continuation-in-part of Ser. No. 332,697, Apr. 3, 1989, abandoned.

[30] Foreign Application Priority Data

Dec. 23, 1988 [DK] Denmark .................. 7215/88
Sep. 28, 1989 [DK] Denmark .................. 4777/89

[51] Int. Cl.⁶ .................. C07K 14/62; A61K 38/28
[52] U.S. Cl. .................. 514/3; 530/303
[58] Field of Search .................. 514/3; 530/303

[56] References Cited

U.S. PATENT DOCUMENTS

| | | |
|---|---|---|
| 3,903,069 | 9/1975 | Gregory et al. |
| 4,320,196 | 3/1982 | Morihara et al. |
| 4,701,440 | 10/1987 | Grau . |
| 4,992,417 | 2/1991 | Katsoyannis . |

FOREIGN PATENT DOCUMENTS

| | | |
|---|---|---|
| A-49226/90 | 8/1990 | Australia . |
| 0 055 945 | 7/1982 | European Pat. Off. . |
| 0 163 529 | 12/1985 | European Pat. Off. . |
| 0 195 691 | 9/1986 | European Pat. Off. . |
| 0 214 826 | 3/1987 | European Pat. Off. . |
| 0 254 516 | 1/1988 | European Pat. Off. . |
| 0 383 472 | 8/1990 | European Pat. Off. . |
| WO 86/05497 | 9/1986 | WIPO . |
| WO 88/06599 | 9/1988 | WIPO . |
| WO 89/10937 | 11/1989 | WIPO . |

OTHER PUBLICATIONS

Chance, "Insulin Analogs", Conference on Insulin, p. 14, (1989).
Nicol et al., "Nature", vol. 4736, pp. 483–485 (1960).
Frank, "Conference on Insulin," pp. 13–14 (1989).
Nakagawa et al., "J. Biol. Chem.", vol. 262, pp. 12054–12058 (1987).
Kobayashi et al., "Biomed. Res. 5", pp. 267–272 (1984).
Shoelson et al., "Proc. Natl. Acad. Sci.", pp. 7390–7394 (1983).
Marki et al., "Hoppe–Seyler's Z. Physiol. Chem.", pp. 1619–1632 (1979).
Morihara, "Nature", vol. 280, pp. 412–413 (1979).
Brange et al., "Protein Engineering", vol. 3, p. 238 (1987).

*Primary Examiner*—Marian C. Knode
*Assistant Examiner*—Benet Prickril
*Attorney, Agent, or Firm*—Steve T. Zelson, Esq; Elies J. Lambiris, Esq

[57] ABSTRACT

Human insulin analogues having a positively charged amino acid residue, i.e. Lys or Arg, in position B28, further being modified in the C-terminal end of the B-chain from $Phe^{B24}$ to the C-terminal amino acid residue and wherein A18, A21 and/or B3 is different from Asn as well as insulin preparations containing the human insulin analogues are provided.

17 Claims, 6 Drawing Sheets

```
        10          20          30          40          50          60
         |           |           |           |           |           |
GAATTCCATTCAAGAATAGTTCAAACAAGAAGATTACAAACTATCAATTTCATACACAAT 70          80          90         100         110         120
         |           |           |           |           |           |
ATAAACGACCAAAAGAATGAAGGCTGTTTTCTTGGTTTTGTCCTTGATCGGATTCTGCTG
                    METLysAlaValPheLeuValLeuSerLeuIleGlyPheCysTrp 130         140         150         160         170         180
         |           |           |           |           |           |
GGCCCAACCAGTCACTGGCGATGAATCATCTGTTGAGATTCCGGAAGAGTCTCTGATCAT
AlaGlnProValThrGlyAspGluSerSerValGluIleProGluGluSerLeuIleIle 190         200         210         220         230         240
         |           |           |           |           |           |
CGCTGAAAACACCACTTTGGCTAACGTCGCCATGGCTAAGAGATTCGTTAACCAACACTT
AlaGluAsnThrThrLeuAlaAsnValAlaMETAlaLysArgPheValAsnGlnHisLeu 250         260         270         280         290         300
         |           |           |           |           |           |
GTGCGGTTCCCACTTGGTTGAAGCTTTGTACTTGGTTTGCGGTGAAAGAGGTTTCTTCTA
CysGlySerHisLeuValGluAlaLeuTyrLeuValCysGlyGluArgGlyPhePheTyr 310         320         330         340         350         360
         |           |           |           |           |           |
CACCAAGGCTGCTAAGGGTATTGTCGAACAATGCTGTACCTCCATCTGCTCCTTGTACCA
ThrLysAlaAlaLysGlyIleValGluGlnCysCysThrSerIleCysSerLeuTyrGln 370         380         390         400
         |           |           |           |
ATTGGAAAACTACTGCAGCTAGACGCAGCCCGCAGGCTCTAGA
LeuGluAsnTyrCysSer
```

*FIG. 3*

INSULIN ANALOGS HAVING A MODIFIED B-CHAIN

This application is a continuation of application Ser. No. 08/275,196 filed on Jul. 14, 1994, now abandoned, which is a continuation of Ser. No. 07/976,805 filed Nov. 16, 1992, now abandoned, which is a continuation-in-part of U.S. Ser. No. 07/453,445 filed Dec. 20, 1989, now U.S. Pat. No. 5,164,366, which is a continuation-in-part of U.S. Ser. No. 07/416,218 filed Oct. 2, 1989, now abandoned, and of U.S. Ser. No. 07/332,697 filed Apr. 3, 1989, now abandoned.

BACKGROUND OF THE INVENTION

1. Technical Field

The present invention relates to novel human insulin analogues exhibiting a low ability to associate in solution, insulin preparations containing the human insulin analogues of this invention and a method of treating Diabetes Mellitus using these human insulin analogues.

2. Background Art

Ever since the discovery of insulin in 1922 many different types of insulin preparations have been used for the treatment of Diabetes mellitus. At the beginning, exclusively insulin solutions exhibiting a rapidly commencing and relatively rapidly ceasing insulin activity were used, but later on insulin preparations exhibiting a wider profile of activity procured by lowering the solubility of insulin by means of additions as, for example, zinc salt and/or protamines have been produced. For reasons of availability, the insulin used herefor has normally been recovered from Pancreas from domestic animals, most frequently oxes, pigs and sheep. However, recently preparations containing human insulin of biotechnological origin have also appeared on the market.

The structure of human insulin is shown in the following formula

When such an insulin is dissolved at a physiological pH value, a concentration-dependent association equilibrium is established between monomeric, dimeric, tetrameric, hexameric And even polymeric insulin. The equilibrium can, for example, be determined by ultracentrifugation, by osmometry or by gel filtration methods, vide, for example, Valdes and Ackers, "Methods in enzymology" vol. 61 (Enzyme Structure, part H. eds.: Hirs & Timasheff), Academic Press 1979, pages 125–142. In normal formulations of insulin preparations, this equilibration is shifted in such a way that the insulin to a very high degree is on a hexameric form.

Substitutions in the insulin molecule can be introduced with the purpose of improving the profile of activity of the insulin in the treatment of Diabetes. Thus, International Patent Application No. WO 86/05497 discloses that one or more substitutions of Glu in the insulin molecule by a neutral amino acid residue causes a shifting of the zone of precipitation of the insulin in such a way that, after injection, a slow release is obtained.

Moreover, European Patent Application No. 214,826 discloses insulin analogues being particularly rapidly absorbed after injection. This effect is a result of the fact that by means of certain substitutions in particular in the B9–B12 region and in the B26–B28 positions in the insulin molecule a suppression of the association tendency of the insulin is obtained so that it is essentially present as monomer or dimer. However, a number of these insulin analoguss exhibits a reduced biological activity.

Throughout the years, a large number of artificially prepared analogues of human insulin has been described, usually with the purpose of elucidating the influence of the structure on the activity, vide, for example, Märke et al., *Hoppe-Seyler's Z. Physiol. Chem.* 360 (1979), 1619–1632. Investigations of the influence of substitutions in the (B22–B26)-sequence of the insulin on the receptor binding have been of particular interest, as said sequence is consid-

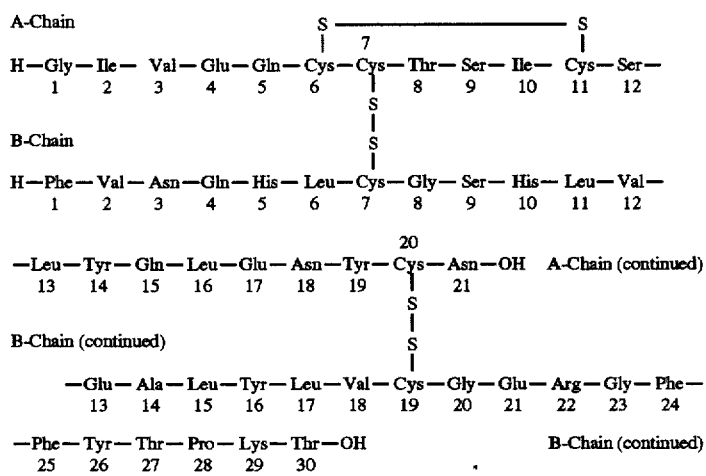

The insulins from certain domestic animals are very similar in structure to human insulin. Thus dog and pig insulin differ from human insulin only by containing Ala in position 30 in the B-chain and rabbit insulin only by containing Ser in the same position. These insulins may be converted into human insulin by replacement of the B30-amino acid residue with Thr by semisynthetic procedures as described by Morihara et al., *Nature* 280 (1979), 412–413 and Marcussen (U.S. Pat. No. 4,343,898).

ered to be an essential site of binding for the insulin receptor, and as naturally occurring mutations have been found with substitutions in said site, vide, for example, Shoelson et al. *PNAS* 80 (1983), 7390–7394 and Kobayashi et al.: *Biomed. Res.* 5 (1984), 267–272. Very low biological activities were found for analogues in which $Phe^{B24}$ or $Phe^{B25}$ are substituted and, therefore, it was concluded that the presence of these two amino acids is of decisive importance to the receptor binding.

DISCLOSURE OF THIS INVENTION

The present invention is based on the surprising recognition that certain human insulin analogues in which one of the amino acid residues Phe$^{B24}$, Phe$^{B25}$, Tyr$^{B26}$, Thr$^{B27}$ or Pro$^{B28}$ is not present, exhibit a low association tendency in solution and at the same time exhibits an unchanged or even higher in vitro biological activity than human insulin. The deletion of either Phe$^{B24}$, Phe$^{B25}$, Tyr$^{B26}$, Thr$^{B27}$ or Pro$^{B28}$ will have the effect that Lys$^{B29}$ is transferred into Lys$^{B28}$. The position of a positive charge in this position in the human insulin molecule is considered to be the important aspect of the present invention. In addition, the insulin derivatives of this invention have been stabilized by substituting Asn in one or more of the positions A18, A21 and/or B3 with another amino acid residue.

SUMMARY OF THE INVENTION

In its broadest aspect, the present invention is related to human insulin analogues in which there is a positively charged amino acid residue, i.e. Lys or Arg, in the position B28, i.e. in position 8 in the B-chain calculated from Gly$^{B20}$.

Surprisingly, the present insulin analogues have a low association tendency resulting in a rapid subcutaneous absorption. At the same time, the compounds of this invention show an increased physical stability compared to other insulin analogues with low association tendency. Introduction of a positive charge in position B28 may be accomplished in two ways. Either by deleting one of the amino acid residues in position B24, B25, B26, B27 or B28 in the human insulin molecule leading to a human insulin analogue with Lys in position B28 or by substituting Pro$^{B28}$ in the human insulin molecule with Lys or Arg. If Arg is preferred in position B28, the deletion of one of the amino acid residues in position B24, B25, B26, B27 or B28 may furthermore be combined with a substitution of the original Lys$^{B29}$ with Arg.

The present human insulin analogues may, furthermore, contain one or more modifications in the C-terminal end of the B-chain compared to human insulin. Thus, the amino acid residues in position B25 to B27 and the amino acid residue(s) following Lys$^{B28}$ or Arg$^{B28}$ may be arbitrarily chosen among the naturally occurring amino acid residues or B29 or B30 or both may be lacking.

According to one aspect of the present invention, Tyr$^{B26}$ may be substituted by another uncharged amino acid residue wherein the second carbon atom in the side chain (Cγ) is sp$^2$-hybridized (the bonds having a planar structure).

The present human insulin analogues can be characterized by the following formula I

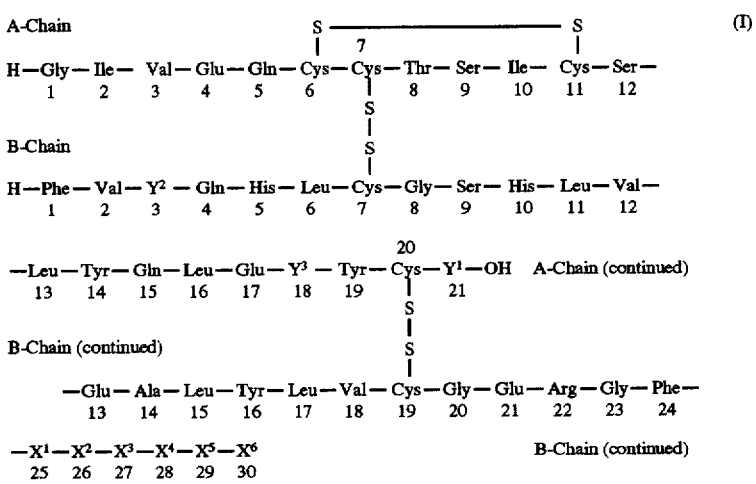

wherein $X^1$, $X^2$, $X^3$, $X^5$, $Y^1$, $Y^2$ and $Y^3$ is any naturally occurring amino acid residue, $X^4$ is Lys or Arg, $X^6$ is any naturally occurring amino acid residue carrying the C-terminal hydroxy group or hydroxy, or $X^5$ and $X^6$ together form the C-terminal hydroxy group.

In an embodiment of this invention, $X^5$ is selected from the group consisting of any naturally occurring amino acid residue except Pro.

In the above formula I, $Y^1$, $Y^2$ and $Y^3$ may independently of each other, in one embodiment, be selected from the group consisting of any naturally occurring amino acid residue except Asn.

In the above formula I, $X^1$ may more specifically be Phe, Ala, His, Thr, Ser, Asn or Tyr, $X^2$ may more specifically be Tyr, Thr, Glu, Asp, Ala, His, Ser or Phe, $X^3$ may more specifically be Pro, Glu, Asp, Ser, Thr or His, $X^5$ may more specifically be Lys, Thr, Ser, Ala, Asp or Glu, $X^6$ may more specifically be Thr—OH, Ser—OH, Ala—OH, Asp—OH, Glu—OH or hydroxy, $Y^1$ may be Asn, Glu, Asp, His, Ser, Thr, Val, Leu, Ile, Ala, Met, Trp, Tyr, Gln or Gly, more preferably Gly, Asp, Glu or Ala, $Y^2$ may be Asn, Glu, Asp, His, Ser, Thr, Val, Leu, Ile, Ala, Met, Trp, Tyr, Gln or Gly, more preferably Glu, Asp or Thr and $Y^3$ may be Asn, Glu, Asp, His, Ser, Thr, Val, Leu, Ile, Ala, Met, Trp, Tyr, Gln or Gly, more preferably Gly, Asp, Glu or Ala.

One group of the present human insulin analogues can be characterized as such in which one of the amino acid residues in position B24 or B25 has been deleted, that the amino acid residue in position B26, optionally, is substituted by another uncharged amino acid residue in which the carbon atom in the γ-position is sp$^2$-hybridized, that, optionally, one or more of the amino acid residues in positions A21, B3 and B30 differ from the amino acid residue in the corresponding positions in human insulin, and that, optionally, no amino acid residue is present in position B30.

According to a more simple definition such analogues are human insulin analogues in which Tyr$^{B26}$ is not present, in which Phe$^{B25}$ has optionally been substituted by another uncharged amino acid residue in which the carbon atom in the γ-position is sp²-hybridized, in which one or more of the amino acid residues in positions A21, B3 and B30, optionally, differ from the amino acid residues in human insulin and in which optionally no amino acid residue is present in position B30.

Examples of uncharged amino acid residues in which $C^\gamma$ is sp²-hybridized are Tyr, Phe, His, Trp and Asn.

It is possible to introduce further substitutions or derivatizations in the human insulin analogues mentioned above if the properties do not change substantially. Such further derivatizations could be esterification or amidation of carboxyl groups, acylation or alkylation of amino or hydroxyl groups or could be deamidation of carboxamide groups. Further substitutions may be exchange of Thr in the A8 position with His or of His in the B10 position with Asp. Moreover, it is possible to add or delete a single or a few amino acid residues at the C- and/or the N-terminal of preferably the B-chain.

One group of the human insulin analogues according to this invention will have the structure shown in formula II below, where W means Tyr, His, Phe or Asn, X means Thr, Ser, Ala, Asp or Glu or a deletion and where optionally one or more of the underscored Asn have been changed to another amino acid residue, for example, Asp by substitution or deamidation or the underscored Asn in the A21 position may be Gly.

Preferred human insulin analogues according to this invention are the following:
des[Phe$^{B25}$] human insulin,
des[Tyr$^{B26}$] human insulin,
des[Thr$^{B27}$] human insulin,
des[Pro$^{B28}$] human insulin,
des[Phe$^{B25}$] porcine insulin,
des[Pro$^{B28}$] porcine insulin,
des[Pro$^{B28}$] rabbit insulin,
des[Phe$^{B25}$],des[Thr$^{B30}$] human insulin,
des[Tyr$^{B26}$],des[Thr$^{B30}$] human insulin,
[Ser$^{A21}$]-des[Pro$^{B28}$] human insulin,
[Gly$^{A21}$]-des[Pro$^{B28}$] human insulin,
[Gly$^{A21}$]-des[Phe$^{B25}$] human insulin,
[Asp$^{A21}$]-des[Phe$^{B25}$] human insulin,
[His$^{B25}$]-des[Tyr$^{B26}$],des[Thr$^{B30}$] human insulin,
[Asn$^{B25}$]-des[Tyr$^{B26}$],des[Thr$^{B30}$] human insulin,
[Asp$^{A21}$]-des[Phe$^{B25}$],des[Thr$^{B30}$] human insulin,
[Asp$^{B28}$]-des[Phe$^{B25}$] human insulin,
[Asp$^{B3}$]-des[Phe$^{B25}$] human insulin,
[Lys$^{B28}$] human insulin,
[Lys$^{B28}$,Thr$^{B29}$] human insulin,
[Arg$^{B28}$]-des[Lys$^{B29}$] human insulin,
des[Pro$^{B28}$],des[Thr$^{B30}$] human insulin,
[Gly$^{A21}$]-des[Thr$^{B27}$] human insulin,
[Gly$^{A21}$,Thr$^{B3}$]-des[Thr$^{B27}$] human insulin,
[Ala$^{A21}$,Thr$^{B3}$]-des[Thr$^{B27}$] human insulin,
[Gly$^{A21}$,Asp$^{B3}$]-des[Thr$^{B27}$] human insulin,
[Ala$^{A21}$,Asp$^{B3}$]-des[Thr$^{B27}$] human insulin and
des[Thr$^{B27}$],des[Thr$^{B30}$] human insulin.

The human insulin analogues according to the present invention may advantageously be used in the treatment of Diabetes as the decreased ability to association leads to a faster uptake in the bloodstream than an ordinary insulin, not only after the normally used subcutaneous injection but also by non-parenteral use, vide, for example, International Patent Application No. WO 87/06137. Also their improved physical stability will make them more advantageous in the Diabetes treatment.

The insulin analogues according to the present invention may be prepared by altering the proinsulin gene through replacement of codon(s) at the appropriate site in the native human proinsulin gene by codon(s) encoding the desired amino acid residue substitute(s) and/or by deleting the codon(s) corresponding to the desired deletion(s). Alternatively, the whole DNA-sequence encoding the

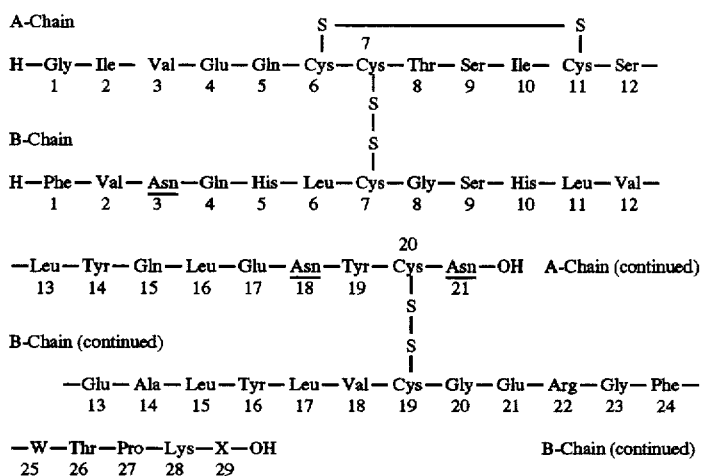

desired insulin analogue may be synthesized. The gene encoding the desired insulin analogue is then inserted into a suitable expression vector which when transferred to a suitable host organism, for example, E. coli, Bacillus or yeast, generates the desired product. The expressed product is then isolated from the cells or the culture broth depending on whether the expressed product is secreted from the cells or not.

The novel insulin analoguss may also be prepared by chemical synthesis by methods analogue to the method described by Märki et al. (Hoppe-Seyler's Z. Physiol. Chem., 360 (1979), 1619-1632). They may also be formed from separately in vitro prepared A- and B-chains containing the appropriate amino acid residue substitutions and deletions, whereupon the modified A- and B-chains are linked together by establishing disulphide bridges according to known methods (for example Chance et al., In: Rick D H, Gross E (eds) Peptides: Synthesis—Structure—Function. Proceedings of the seventh American peptide symposium, Illinois, pp. 721-728).

The insulin analogues may furthermore be prepared by a method analogue to the method described in European Patent Application No. 163,529, the disclosure of which is incorporated by reference hereinto. By such method, an insulin precursor of the human insulin analogue wherein the basic amino acid in position B28 or B29 (if the final product shall have a basic amino acid in this position) is connected to Gly$^{A1}$ by means of either a peptide bond or a peptide chain of varying length, is expressed and secreted by yeast with correctly positioned disulphide bridges and is then converted into the desired human insulin analogue by the Morihara method (Morihara supra) or the so-called transpeptidation reaction (see U.S. Pat. No. 4,343,898).

Accordingly, the present insulin analogues may be prepared by inserting a DNA-sequence encoding a precursor of the insulin analogue in question into a suitable yeast expression vehicle which, when transferred to yeast is capable of expressing and secreting the precursor of the insulin analogue in which Lys$^{B28}$, Arg$^{B28}$, Lys$^{B29}$ or Arg$^{B29}$ is connected to Gly$^{A1}$ by a peptide bond or a peptide chain with the formula III

$$—R_n—R^1—\qquad\qquad (III)$$

wherein R is a peptide chain with n amino acid residues, n is an integer from 0 to 33, and R$^1$ is Lys or Arg, when culturing the transformed yeast strain in a suitable nutrient medium. The precursor is then recovered from the culture broth and reacted with an amino compound with the formula IV

$$Q—OR"\qquad\qquad (IV)$$

wherein Q is a single amino acid residue, preferably Thr, or a dipeptide, and R" is a carboxy protecting group (for example, methyl or tert-butyl), using trypsin or trypsin-like enzyme as a catalyst in a mixture of water and organic solvents analogously as described in U.S. Pat. No. 4,343,898 (the disclosure of which is incorporated by reference hereinto) whereupon the carboxy protecting group is removed and the insulin analogue is isolated from the reaction mixture.

If the insulin analogues contain an amino acid residue different from Lys or Arg as the C-terminal residue in the B-chain, they may also be prepared by a method analogue to the method described in European Patent Application. No. 195,691 the disclosure of which is incorporated by reference hereinto. By this method, insulin analogue precursors of the type having a bridge between the A- and B-chain consisting of a single pair of basic amino acid (Lys, Arg) are made in yeast and then converted into the insulin analogue by an enzymatic conversion.

If the C-terminal amino acid residue in the B-chain is Lys or Arg, then the insulin analogues can be prepared from the above biosynthetic precursors by enzymatic cleavage with trypsin.

Human insulin analogues of this invention in which substitutions are only present within the last amino acid residues nearest to the C-terminal of the B-chain, may moreover be prepared in a manner known per se from, for example, porcine insulin as described in Inoye et al.; *JACS* 101, (1979), 751-752, whereby the porcine insulin is first split with trypsin to des-(B23-30) human insulin, whereupon the latter, also enzymatically, is coupled with a synthetic peptide having the desired amino acid sequence.

The present insulin analoguss maybe used for the preparation of novel insulin preparations with insulin activity to be substituted for human or porcine insulin in the insulin preparations heretofore known to the art. Such novel insulin preparations contain the insulin analogues according to the present invention or a pharmaceutically acceptable salt thereof in aqueous solution or suspension, preferably at neutral pH. The aqueous medium is made isotonic, for example, with sodium chloride, sodium acetate or glycerol. Furthermore, the aqueous medium may contain zinc ions, buffers such as acetate and citrate and preservatives such as m-cresol, methylparaben or phenol. The pH value of the preparation is adjusted to the desired value and the insulin preparation is made sterile by sterile filtration.

The present insulin analoguss may also be mixed with other insulin analoguss having a protracted insulin activity to prepare insulin preparations consisting of a mixture of rapid acting and protracted insulin.

The insulin preparations of this invention can be used similarly to the use of the known insulin preparations.

TERMINOLOGY

The abbreviations used for the amino acids are those stated in *J. Biol. Chem.* 243 (1968), 3558. The amino acids are in the L configuration. Unless otherwise indicated, the species of insulins stated herein is human.

BRIEF DESCRIPTION OF THE DRAWINGS

This invention is further illustrated with reference to the accompanying drawings in which FIG. 3 shows the DNA sequence of the 0.4 kb EcoRI-XbaI fragment from the plasmid pKFN-864.

DETAILED DESCRIPTION

Figure 1:
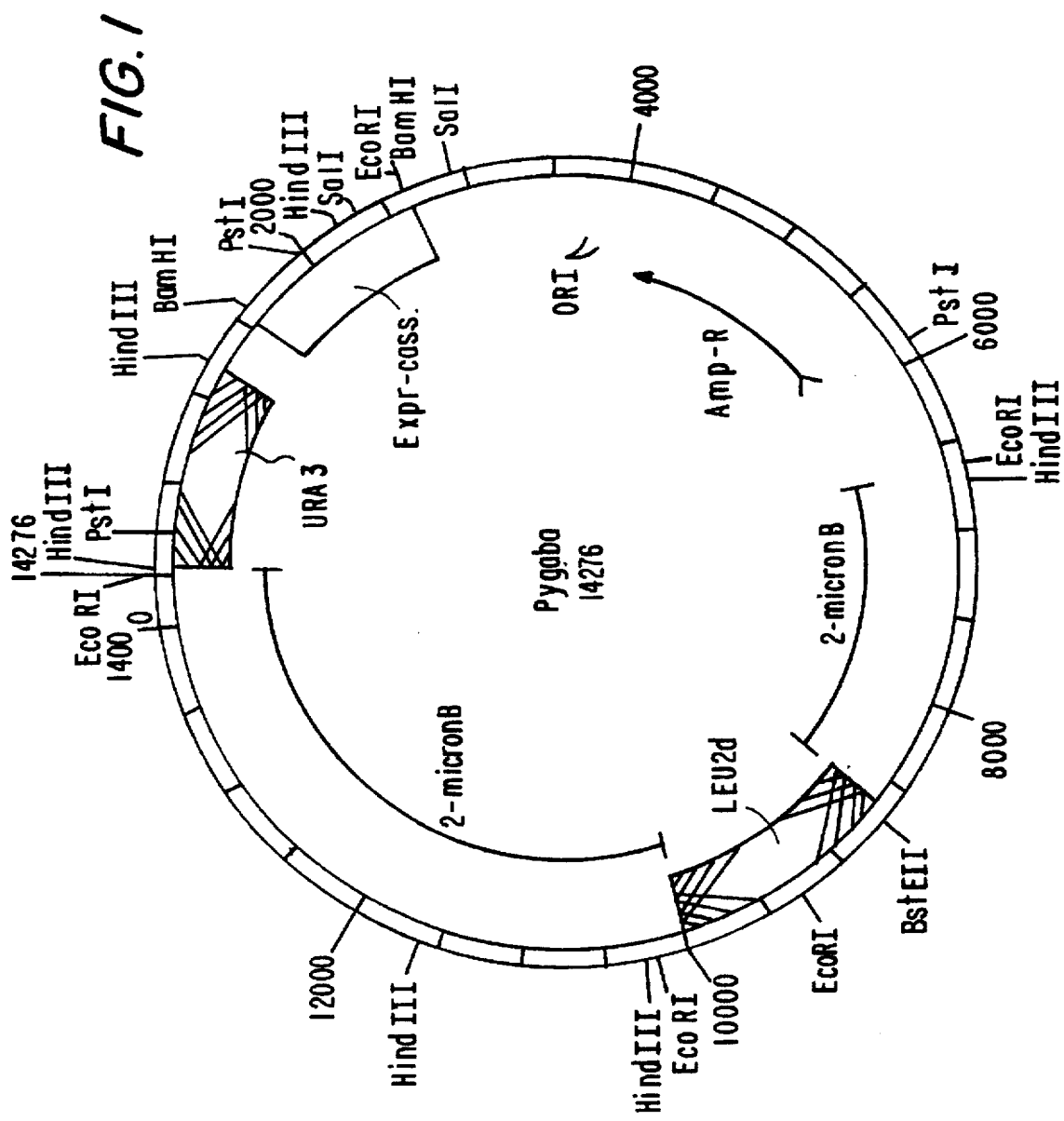
FIG. 1 shows the expression plasmid pYGABA 14276.

DNA-sequences encoding modified insulin precursors were constructed with basis in the expression cassette, which is contained in the BamHI restriction fragment from the expression plasmid pYGABA as shown in FIG. 1, has a length of 1103 base pairs and contains essentially the following (listed in succession starting from the 5'-end):The GAPDH promoter (Travis et al., *J. Biol. Chem.*, 260 (1985), 4384–4389) followed by the coding region consisting of: The 83 N-terminal amino acids of the MF α1-leader sequence encoded by the wild-type yeast DNA-sequence as described by Kurjan & Herskowitz followed by the two codons AAA and AGA encoding Lys and Arg and again followed by the coding region for the insulin precursor single chain desThr$^{B30}$ human insulin (SCI), which is a synthetically constructed gene using preferred yeast codons. After two stop-codons, a SalI restriction site is positioned, and the rest of the sequence constitutes the MFα1-sequence containing the terminator region. The sequence is constructed using entirely standard techniques.

The method employed was "oligonucleotide site directed mutagenesis", which is described by Zoller & Smith, *DNA*, 3, (1984), 479–488. The method is briefly described in the following, and is described thoroughly in Example 1. The insulin precursor sequence is isolated from the expression plasmid and inserted into a single-stranded genom, circular M13 bacteriophage vector. A chemically synthesized complementary DNA-strand is then annealed to the single-stranded genom. The DNA-strand contains the desired sequence surrounded by sequences completely homologous to insulin sequences on the circular DNA. The primer is then extended in vitro into the entire length of the circular genom biochemically using Klenow polymerase. This strand will give rise to single-stranded phages, which when grown in *E. coli* give the possibility of isolating double-stranded DNA with the desired sequence. From this double-stranded DNA, a restriction fragment can be isolated and reinserted into the expression vector.

MODES FOR CARRYING OUT THE INVENTION

This invention is further illustrated by the following Examples.

EXAMPLE 1

Construction of an expression plasmid, which can be used to express des[Phe$^{B25}$] SCI The expression cassette, which is contained in the expression plasmid pYGABA (shown in FIG. 1) on a BamHI restriction fragment, was isolated: The expression plasmid was incubated with the restriction endonuclease BamHI. The conditions were: 20 µg of plasmid, 50 units of BamHI, 100 mM NaCl, 50 mM TRIS HCl (TRIS=tris (hydroxymethyl)aminomethane), pH 7.5, 10 mM MgCl$_2$, and 1 mM DTT in a volume of 100 µliters. The temperature was 37° C. and the reaction time 2 hours. The two DNA-fragments were separated on a 1% agarose gel, and the desired fragment was isolated.

Ligation to the M13 vector M13mp18:

The isolated restriction fragment was ligated to the bacteriophage vector M13mp18 also cut with the restriction endonuclease BamHI in the following reaction mixture: Fragment 0.2 µg, vector 0.02 µg, 50 mM TRIS HCl, pH 7.4, 10 mM MgCl$_2$, 10 mM DTT and 1 mM ATP in a volume of 20 µliters. 5 µliters of this mixture were transformed into the *E. coli* strain JM101. The presence of fragment in the vector and the orientation of the fragment was determined by restriction enzyme mapping on double-stranded M13-DNA isolated from the transformants.

Isolation of single-stranded (ss) DNA (template):

From the transformant described above ss-DNA was isolated according to a method described by Messing in Gene, 19 (1982), 269–276.

5'phosphorylatipn of the mutagenization primer:

The mutagenization primer with the sequence 5'-TTGGAGTGTAGAAACCTCTT-3' was phosphorylated in the 5' end in a 30 µliters reaction mixture containing 70 mM TRIS HCl, pH 7.0, 10 mM MgCl$_2$, 5 mM DTT, I mM ATP, 100 pmol oligonucleotide and 3.6 units of T4 polynucleotide kinase. The reaction was carried out for 30 min. at 37° C. Then, the enzyme was inactivated by incubating the mixture for 10 min. at 65° C.

Annealing of template and phosphorylated mutagenization primer:

Annealing of template and primer was carried out in a 10 µliters volume containing 0.5 pmol template, 5 pmol primer, 20 mM TRIS HCl, pH 7.5, 10 mM MgCl$_2$, 50 mM NaCl and 1 mM DTT by heating for 10 min. at 65° C. and cooling afterwards to 0° C.

Extension/ligation reaction:

To the reaction mixture above, 10 µliters of the following mixture were added: 0.3 mM dATP, 0.3 mM dCTP, 0.3 mM dGTP, 0.3 mM TTP, 1 mM ATP, 20 mM TRIS HCl, pH 7.5, 10 mM MgCl$_2$, 10 mM DTT, 3 units of T4 DNA ligase and 2.5 units of Klenow polymerase. Then, the reaction was carried out for 16 hours at 16° C.

Transformation of JM101:

The reaction mixture above was transformed in different dilutions into CaCl$_2$ treated *E. coli* JM101 cells using standard techniques and plated in 2×YT topagar on 2×YT agar plates. (2×YT=tryptone 16 g/liter, yeast extract 10 g/liter, NaCl 5 g/liter. 2×YT topagar=2×YT with 0.4% agarose added and autoclaved. 2×YT agar plates=2×YT with 2% agar added and autoclaved). The plates were incubated at 37° C. overnight.

Identification of positive clones:

The method used was plaque-lift hybridization which is described in the following: a nitrocellulose-filter was placed on a plate with a suitable plaque-density, so that the filter was wetted. The filter was then bathed in the following solutions: 1.5M NaCl, 0.5M NaOH for 30 sec., 1.5M NaCl, 0.5M TRIS HCl, pH 8.0 for 1 min., 2×SSC (0.3M NaCl, 0.03M sodium citrate) till later use. The filter was dried on 3 MM filter paper and baked for 2 hours at 80° C. in a vacuum oven.

The mutagenization primer with the sequence 5'-TTGGAGTGTAGAAACCTCTT-3' was labelled radioactively in the 5' end in a 30 µliters volume containing 70 mM TRIS HCl, pH 7.5, 10 mM MgCl$_2$, 5 mM DTT, 10 pmol oligonucleotide, 20 pmol γ-$^{32}$P-ATP and 3.5 units of T4 polynucleotide kinase. The mixture was incubated at 37° C. for 30 min. and then for 5 min. at 100° C.

The dried filter was prehybridized for 2 hours at 65° C. in 6×SSC, 0.2% bovine-serum albumin, 0.2% Ficoll, 0.2% polyvinylpyrrolidone, 0.2% sodium dodecyl sulphate (SDS) and 50 µg/ml salmon-sperm DNA. Then, the reaction mixture containing the labelled probe was added to 15 ml of fresh prehybridization mix, and the filter was bathed herein overnight at 28° C. with gentle shaking. After hybridization the filter was washed 3 times for each 15 min. in 2×SSC+ 0.1% SDS and autoradiographed. After wash in the same solution, but now at 52° C., and another autoradiography, plaques containing DNA-sequences complementary to the mutagenization primer were identified.

Re-screening of positive clones:

Because the identified clone is a result of a heteroduplex, the plaque was plated again. The hybridization and identification were repeated.

Purification of double-stranded M13-phage DNA:

A re-screened clone was used for infection of the *E. coli* strain JM101. A culture containing approximately 10$^8$ phages and 5 colonies of JM101 was grown for 5 hours in a 5 ml 2×YT medium at 37° C. Then, double-stranded, circular DNA was purified from the pellet according to a method described by Birnboim & Doly, Nucleic Acids Res., 2 (1979), 1513.

Isolation of a restriction fragment containing modified insulin precursor:

The DNA-preparation (appr. 5 µg) isolated above was digested with 10 units of the restriction endonuclease BamHI in 60 µliters of 100 mM NaCl, 50 mM TRIS HCl, pH 7.5, 10 mM MgCl$_2$ and 1 mM DTT for 2 hours at 37° C. The DNA-products were separated on an agarose-gel, and the fragment was purified from the gel.

Figure 2:
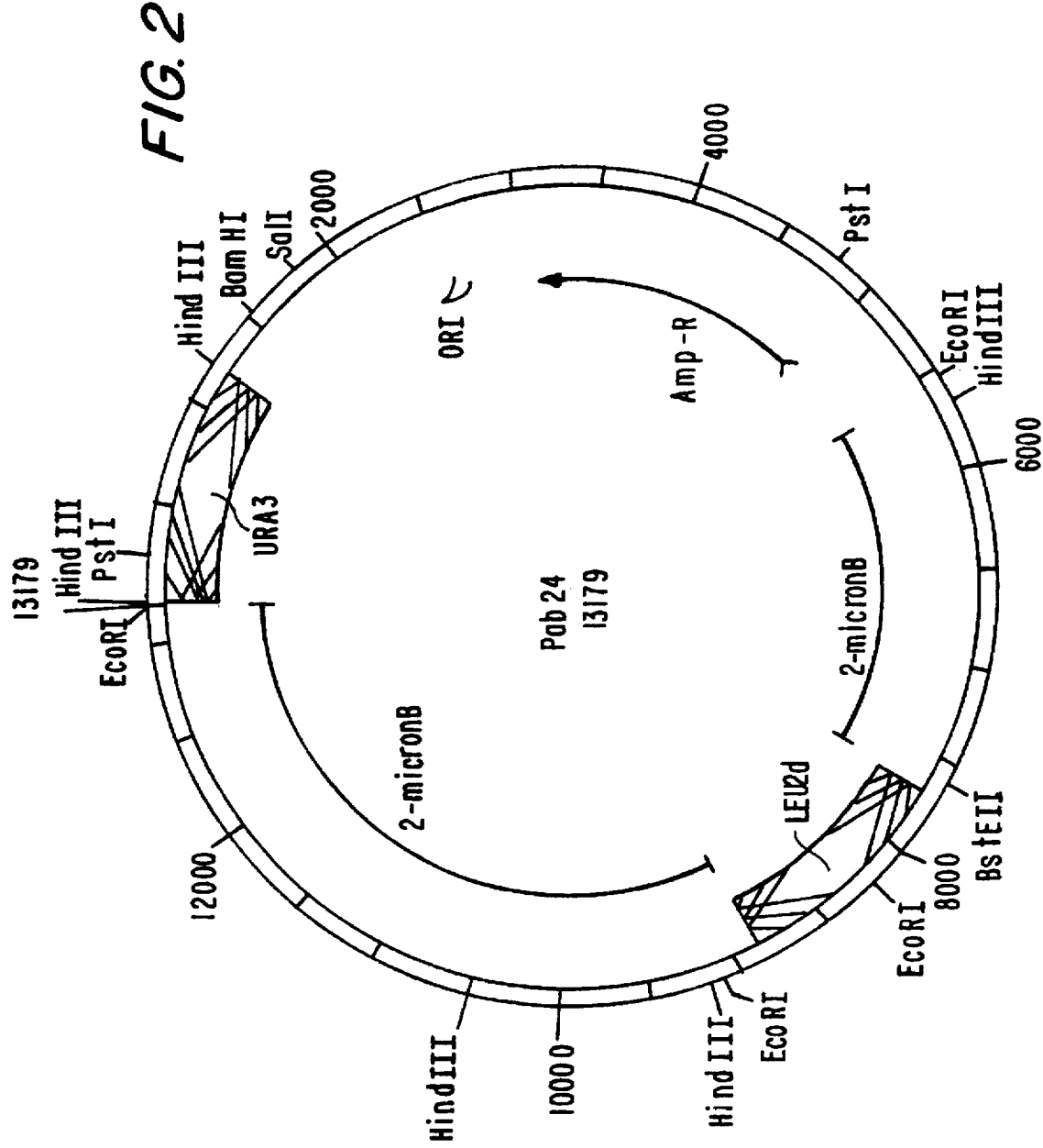
FIG. 2 shows the yeast vector pAB24.

Ligation to the yeast vector pAB24 (FIG. 2):

The isolated restriction fragment was ligated to the yeast vector pAB24 digested with the restriction endonuclease BamHI in the following reaction mixture: Fragment 0.2 µg, vector 0.02 μg, 50 mM TRIS HCl, pH 7.4, 10 mM MgCl$_2$, 10 mM DTT, 1 mM ATP in a total volume of 20 μliters. 5 μliters of this reaction mix was used for transformation of the E. coli strain MC1061, in which the modified expression plasmid was identified and propagated. The plasmid was identical to pYGABA, except for the deleted codon.

Transformation of yeast:

Transformation of the expression plasmid into the yeast strain Saccharomyces cerevisiae JC482ΔpepΔLeu2cir° (α, his4, pep4, ura3, leu2, cir°) was carried out as described by Ito et al., J. Bact., 153, (1983), 163–168. The transformed cells were plated on SC-ura medium (0.7% Yeast Nitrogen Base, 2.0% glucose, 0.5% casamino acids, 2.0% agar) for selection for plasmid containing cells.

EXAMPLE 2

Construction of an expression plasmid, which can be used for production of des[Tyr$^{B26}$] SCI The procedure used was essentially the same as described in example 1, except that the mutagenization primer had the sequence 5'-ACCCTTTGGAGTGAAGAAACCTCT-3', that the hybridization temperature was 36° C., and that the washing temperature after hybridization was 60° C. The modified plasmid has a sequence identical to pYGABA, except for the deleted codon.

EXAMPLE 3

Construction of an expression plasmid, which can be used for production of [His$^{B25}$],des[Tyr$^{B26}$] SCI The procedure used was essentially the same as described in Example 1, except that the mutagenization primer had the sequence 5'-AATACCCTTTGGAGTGTGGAAACCTCT TTCACC-3', that the hybridization temperature was 43° C., and that the washing temperature after hybridization was 66° C. The modified plasmid has a sequence identical to pYGABA, except for the modified and deleted codons.

EXAMPLE 4

Construction of an expression plasmid, which can be used for production of [Asn$^{B25}$],des[Tyr$^{B26}$] SCI The procedure used was essentially the same as described in Example 1, except that the mutagenization primer had the sequence 5'-AATACCCTTTGGAGTGTTGAAACCTCTT TCACC-3', that the hybridization temperature was 42° C., and that the washing temperature after hybridization was 65° C. The modified plasmid has a sequence identical to pYGABA, except for the modified and deleted codons.

EXAMPLE 5

Expression of precursor and isolation from the culture medium

Yeast, transformed as described in Examples 1 to 4, was propagated on Petri-plates containing minimal-medium without uracil for 48 hours at 30° C. 100 ml shake bottles containing minimal-medium without uracil+5 g/liter casamino acids+10 g/liter succinic acid+30 g/liter glucose at pH 5.0 was inoculated with a single colony from the Petri-plate. The bottles were then shaken at 30° C. in incubator for 72 hours.

After centrifugation 1 liter of pooled supernatant was sterilized by filtration and adjusted to pH 4–4.5 and a conductivity<10 mS by addition of 5M HCl and water. With a flow of 120 ml/hour the supernatant was then applied to a 1.6×6 cm column of S/Sepharose®FF previously equilibrated with 50 mM acetic acid, 50% (by volume) ethanol adjusted to pH 4.0 with NaOH. The column was washed with 60 ml buffer and the precursor was then eluted by a linear gradient of NaCl from 0 to 0.35M in 360 ml buffer with a flow of 10 ml/hour. The eluate was divided in fractions of 4 ml and detected for UV-absorbance. Fractions containing precursor were identified by RP-HPLC analysis and were pooled. After desalting on a column of Sephadex®G25 in 1M acetic acid the precursor was isolated by lyophilization.

EXAMPLE 6

Preparation of des[Phe$^{B25}$],des[Thr$^{B30}$] human insulin 400 mg of des[Phe$^{B25}$] SCI, prepared by the methods described in Examples 1 and 5, were dissolved in 40 ml of 50 mM TRIS, 20% (by volume) ethanol adjusted to pH 9 with HCl and 40 ml (settled volume) of Sepharose® containing 32 mg of immobilized trypsin in the same buffer were added. The suspension was left for 24 hours at 8°–10° C. with gentle agitation and was then filtered. The gel was washed with 40 ml of buffer, and the pooled filtrates were applied to a 2.6×7.5 cm column of Q-Sepharose®FF previously equilibrated with 50 mM TRIS, 50% (by volume) ethanol, adjusted to pH 8.0 with HCl. The column was then eluted with a linear gradient of NaCl from 0 to 0.15M in the same buffer over 6 hours with a flow of 225 ml/hour. The eluate was detected for UV-absorbance and fractions containing the main protein peak were pooled. The protein was precipitated at pH 5.4 after removal of the ethanol in vacuo.

250 mg of des[Phe$^{B25}$],des[Thr$^{B30}$] human insulin were isolated by lyophilization.

The identity of the product was confirmed by amino acid analysis, by plasma desorption mass spectrometry and by sequential Edman degradation of the separated vinylpyridylated A- and B-chains.

EXAMPLE 7

Preparation of des[Phe$^{B25}$] human insulin 200 mg of des[Phe$^{B25}$],des[Thr$^{B30}$] human insulin prepared by the methods described in example VI were dissolved in a mixture containing 400 mg of threonine methyl ester, 2.0 ml of ethanol and 0.8 ml of water. The pH value was adjusted to 6.3 with acetic acid and 4 ml (settled volume) of Sepharose® containing 3.2 mg of immobilized trypsin were added. After standing for 2 hours at 20° C. with gentle agitation, the gel was removed by filtration, and the protein was precipitated by addition of 10 volumes of 2-propanol. The air-dried precipitate was redissolved in 20 mM TRIS HCl, 60% (by volume) ethanol, pH 8.25, and applied to a 2.6×20 cm Q-Sepharose®FF column, previously equilibrated with the said buffer, and eluted with a linear NaCl-gradient in the same buffer increasing from 0 to 0.1M over 15 hours at a flow rate of 125 ml/hour. The ethanol was removed in vacuo from the pooled fractions containing desPhe$^{B25}$ human insulin (B30-methyl ester), and the protein was precipitated at pH 6.1. The suspension was centrifugated and the precipitate was lyophilized. The methyl ester was then hydrolyzed for 10 min. in cold 0.1M NaOH at a protein concentration of 10 mg/ml. The reaction was stopped by adjusting the pH value to 8.5, and 2 volumes of 20 mM TRIS HCl, pH 8.5, were added. The solution was then applied to a 2.6×20 cm Q-Sepharose®FF column and eluted as described above. The protein was precipitated at pH 5.5 after removal of the ethanol in vacuo.

80 mg of des[Phe$^{B25}$]-human insulin were obtained after lyophilization.

The identity of the product was confirmed by amino acid analysis, by plasma desorption mass spectrometry and by sequential Edman degradation of the separated vinylpyridylated A- and B-chains.

EXAMPLE 8

Preparation of des[Tyr$^{B26}$],des[Thr$^{B30}$] human insulin 250 mg of des[Tyr$^{B26}$] SCI, prepared by the methods described in the examples II and V, were dissolved in 25 ml of 50 mM TRIS, 20% (by volume) ethanol adjusted to pH 9 with HCl and 25 ml (settled volume) of Sepharose® containing 20 mg of immobilized trypsin in the same buffer were added. The suspension was left for 24 hours at 8°–10° C. with gentle agitation and was then filtered. The gel was washed with 25 ml of buffer, and the pooled filtrates were applied to a 2.6×7.5 cm column of Q-Sepharose®FF previously equilibrated with 50 mM TRIS, 50% (by volume) ethanol, adjusted to pH 8.0 with HCl. The column was then eluted with a linear gradient of NaCl from 0 to 0.15M in the same buffer over 6 hours with a flow of 225 ml/hour. The eluate was detected for UV-absorbance and fractions containing the main protein peak were pooled. The protein was precipitated at pH 5.4 after removal of the ethanol in vacuo.

130 mg of des[Tyr$^{B26}$],des[Thr$^{B30}$] human insulin were isolated by lyophilization.

The identity of the product was confirmed by amino acid analysis and by sequential Edman degradation of the separated vinylpyridylated A- and B-chains.

EXAMPLE 9

Preparation of [His$^{B25}$],des[Tyr$^{B26}$],des[Thr$^{B30}$] human insulin 450 mg of [His$^{B25}$],des[Tyr$^{B26}$] SCI, prepared by the methods described in the Examples 3 and 5, were dissolved in 45 ml of 50 mM TRIS, 20% (by volume) ethanol adjusted to pH 9 with HCl and 45 ml (settled volume) of Sepharose® containing 36 mg of immobilized trypsin in the same buffer were added. The suspension was left for 24 hours at 8°–10° C. with gentle agitation and was then filtered. The gel was washed with 40 ml of buffer, and the pooled filtrates were applied to a 2.6×7.5 cm column of Q-Sepharose®FF previously equilibrated with 50 mM TRIS, 50% (by volume) ethanol, adjusted to pH 8.0 with HCl. The column was then eluted with a linear gradient of NaCl from 0 to 0.15M in the same buffer over 6 hours with a flow of 225 ml/hour. The eluate was detected for UV-absorbance and fractions containing the main protein peak were pooled. The protein was precipitated at pH 5.4 after removal of the ethanol in vacuo.

200 mg of [His$^{B25}$],des[Tyr$^{B26}$],des[Thr$^{B30}$]-human insulin were isolated by lyophilization.

The identity of the product was confirmed by amino acid analysis and by sequential Edman degradation of the separated vinylpyridylated A- and B-chains.

EXAMPLE 10

Preparation of [Asn$^{B25}$],des[Tyr$^{B26}$],des[Thr$^{B30}$] human insulin 150 mg of [Asn$^{B25}$],des[Tyr$^{B26}$] SCI, prepared by the methods described in the Examples 4 and 5, were dissolved in 15 ml of 50 mM TRIS, 20% (by volume) ethanol adjusted to pH 9 with HCl and 15 ml (settled volume) of Sepharose® containing 12 mg of immobilized trypsin in the same buffer were added. The suspension was left for 24 hours at 8°–10° C. with gentle agitation and was then filtered. The gel was washed with 40 ml of buffer, and the pooled filtrates were applied to a 1.6×10 cm column of Q-Sepharose®FF previously equilibrated with 50 mM TRIS, 50% (by volume) ethanol, adjusted to pH 8.0 with HCl. The column was then eluted with a linear gradient of NaCl from 0 to 0.15 in the same buffer over 6 hours with a flow of 90 ml/hours. The eluate was detected for UV-absorbance and fractions containing the main protein peak were pooled. The protein was precipitated at pH 5.4 after removal of the ethanol in vacuo.

80 mg of [Ans$^{B25}$],des[Tyr$^{B26}$],des[Thr$^{B30}$] human insulin were isolated by lyophilization.

The identity of the product was confirmed by amino acid analysis and by sequential Edman degradation of the separated vinylpyridylated A- and B-chains.

EXAMPLE 11

Preparation of [Asp$^{A21}$],des[Phe$^{B25}$],des[Thr$^{B30}$] human insulin 50 mg of des[Phe$^{B25}$],des[Thr$^{B30}$] human insulin prepared by the methods described in Example 6 were dissolved in 10 ml water by adjusting the pH value to 2 with 1M HCl. The solution was then left for 16 days at 30° C. After cooling (to 20° C.) 7.5 g of urea were added and the pH value was adjusted to 8.1 with 1M NaOH. The solution was then applied to a 1.6×20 cm Q-Sepharose®FF column, previously equilibrated with 20 mM TRIS HCl, 7M urea, pH 8.1 at 4° C., and eluted with a linear NaCl gradient in the same buffer increasing from 0 to 0.05M over 24 hours at a flow rate of 40 ml/hour. The pooled fractions containing the protein from the last eluting peak were desalted on a column of Sephadex®G25 in 1M acetic acid and lyophilized.

30 mg of [Asp$^{A21}$],des[Phe$^{B25}$],des[Thr$^{B30}$] human insulin were obtained.

The identity of the product was confirmed by amino acid analysis, by 5-step Edman degradation and by C-terminal analysis using carboxypeptidase A.

EXAMPLE 12

Preparation of [Ser$^{A21}$],des[Pro$^{B28}$] human insulin

Construction of an expression plasmid which can be used for production of [Ser$^{A21}$],des[Pro$^{B28}$] human insulin and preparation of [Ser$^{A21}$],des[Pro$^{B28}$] human insulin.

A pUC-19 derived plasmid, pKFN-864, encoding this analogue was constructed by gapped duplex mutagenesis (Morinaga et al., Biotechnology 2 (1984), 636–639) of plasmid pKFN-734 using the two mutagenic primers NOR-648 CTAGAGCCTGCGGGCTGCGTCTAGCTG-CAGTAG and Nor-745 ATTGTTCGACAATACCCTTAG-CAGCCTTGGTGTAGAAGAAACCTCTTTCACC. Plasmid pKFN-734 was constructed by ligating the 0.4 kb ECoRI-XbaI fragment encoding a synthetic yeast signal-leader fused in-frame frame to a synthetic insulin precursor gene B(1–29)-Ala-Ala-Lys-A(1–21) from plasmid pLaC212spx3 to the 2.7 kb EcoRI-XbI fragment from pUC-19 (Yannisch-Perron et al., Gene 33 (1985), 103–119).

Plasmid pLaC212spx3 is described in Example 3 and in FIGS. 6 and 13 of International Patent Application Publication No. WO 89/02463.

Figure 4A:
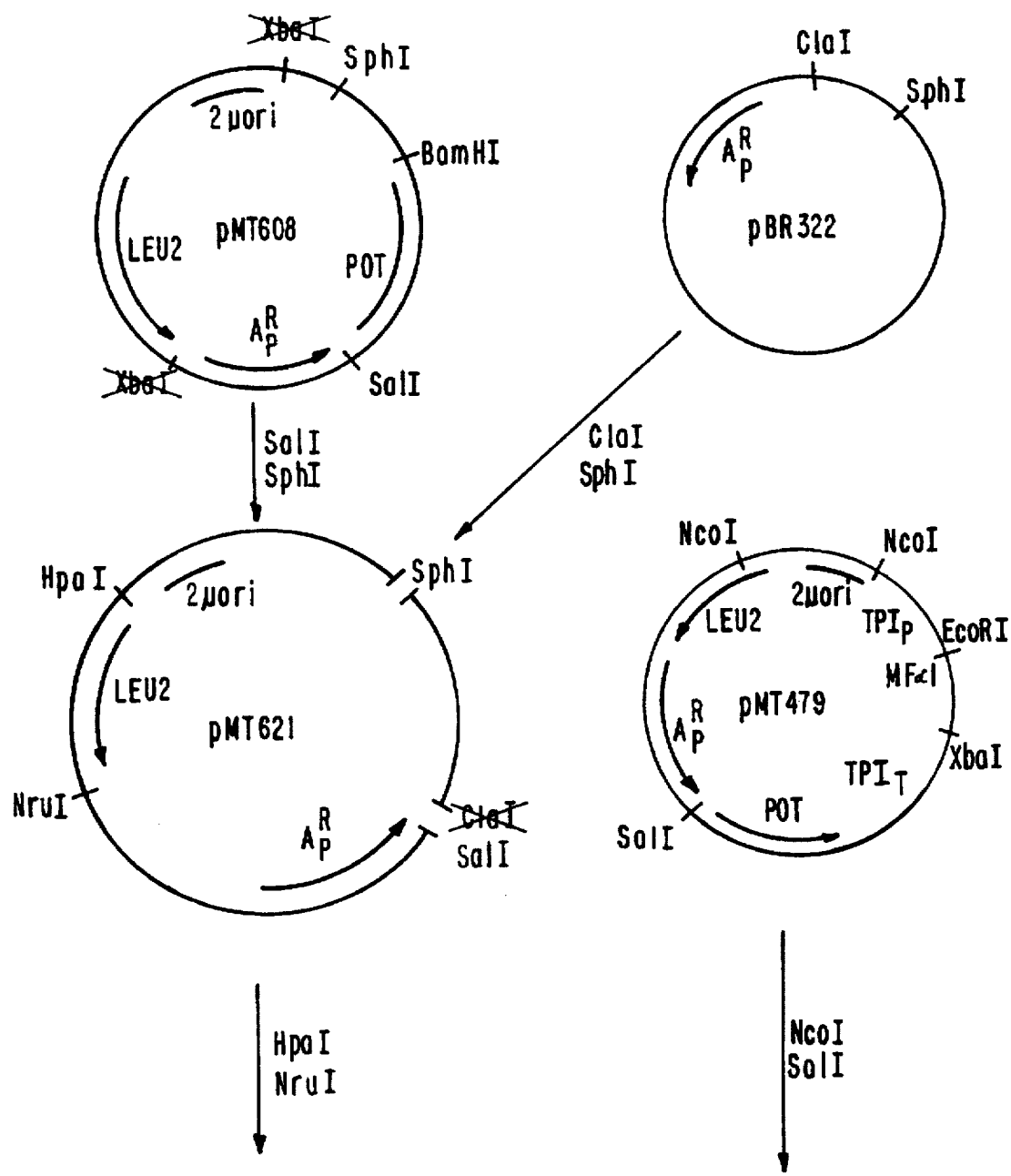
FIG. 4 shows the preparation of the expression plasmid pKFN-866.
Figure 4B:
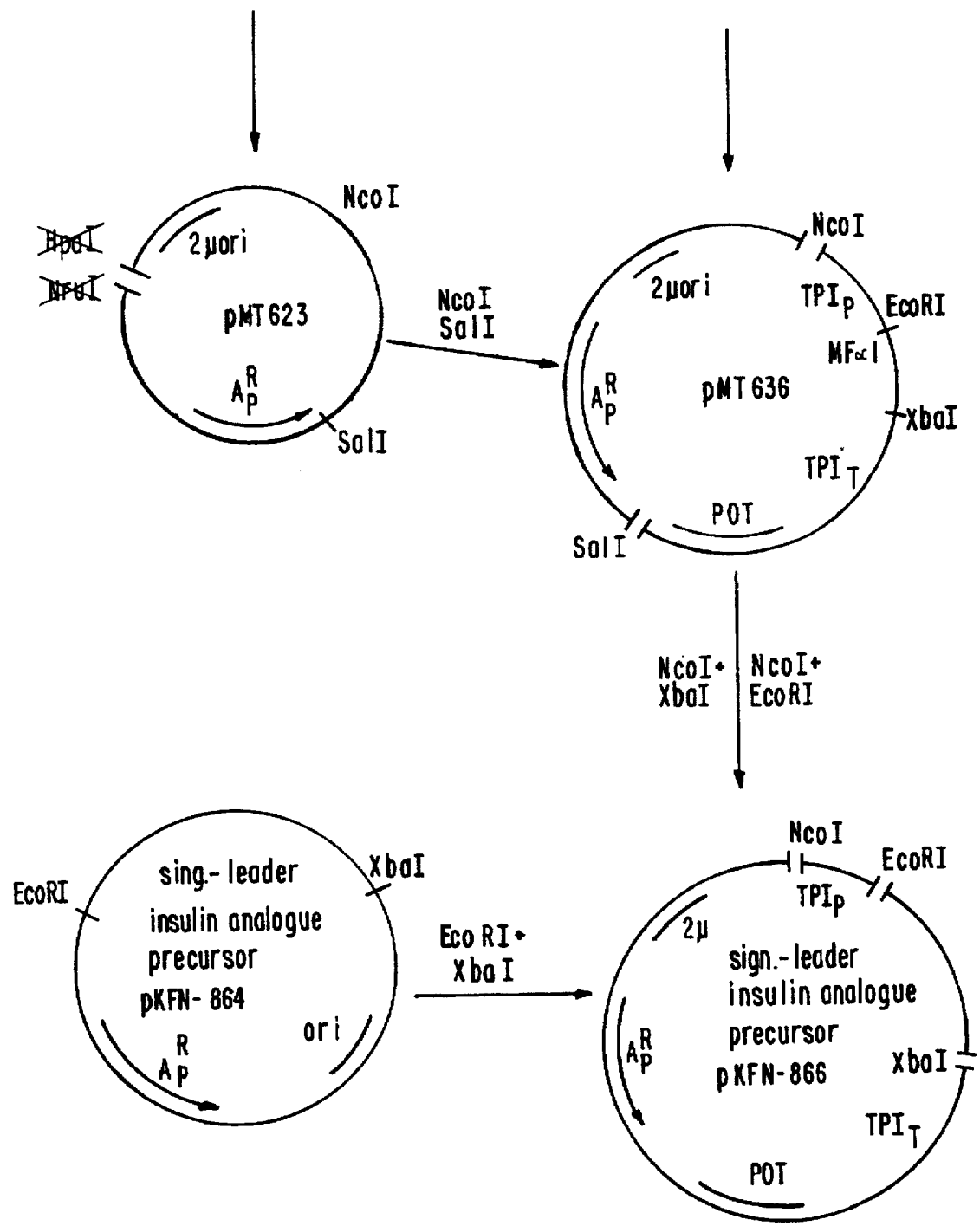

The DNA sequence of the 0.4 kb EcoRI=XbaI fragment from pKFN-864 encoding signal-leader-insulin-B(1–27)-Lys-Ala-Ala-Lys-A(1–20)-Ser is given in FIG. 3.

pKFN-864 was cut with EcoRI and XbaI and the 0.5 kb fragment was ligated to the 9.5 kb NcoI-XbaI fragment from pMT636 and the 1.4 kbNcoI-EcoRI fragment from pMT636, resulting in plasmid pKFN-866, see FIG. 4. Plasmid pHT636 was constructed from pMT608 after deletion of the LEU-2 gene and from pMT479, see FIG. 4. pMT608 is described in European Patent Application 195 691. pMT479 is described in European Patent Application 163 529. pMT479 contains the *Schizosaccharomyces pombe* TPI gene (POT), the *S. cerevisiae* triosephosphate isomerase promoter and terminator, $TPI_P$ and $TPI_T$ (Alber and Kawasaki, *J. Mol. Appl. Gen.* 1 (1982), 419–434). Plasmid pKFN-866 contains the following sequence:

$TPI_P$-signal-leader-insulin-B(1–27)-Lys-Ala-Ala-Lys-A(1–20)-Ser-$TPI_T$.

*S. cerevisiae* strain MT663 (E2-7B XE11-36 a/α, ΔtpiΔtpi, pep 4-3/pep 4-3) was grown on YPGaL (1% Bacto yeast extract, 2% Bacto peptone, 2% galactose, 1% lactate) to an O.D. at 600 nm of 0.6.

100 ml of the resulting culture was harvested by centrifugation, washed with 10 ml of water, recentrifuged and resuspended in 10 ml of a solution containing 1.2M sorbitol, 25 mM $Na_2EDTA$ pH=8.0, and 6.7 mg/ml dithiotreitol. The suspension was incubated at 30° C. for 15 minutes, centrifuged and the cells resuspended in 10 ml of a solution containing 1.2M sorbitol, 10 mM $Na_2EDTA$, 0.1M sodium citrate, pH=5.8, and 2 mg Novozym® 234. The suspension was incubated at 30° C. for 30 minutes, the cells collected by centrifugation, washed in 10 ml of 1.2M sorbitol and 10 ml of CAS (1.2M sorbitol, 10 mM $CaCl_2$, 10 mM TRIS HCl (pH=7.5) and resuspended in 2 ml of CAS. For transformation 0.1 ml of CAS-resuspended cells were mixed with approximately 1 µg of plasmid pKFN-866 and left at room temperature for 15 minutes. 1 ml of (20% polyethyleneglycol 4000, 10 mM $CaCl_2$, 10 mM TRIS HCl, pH=7.5) was added and the mixture left for further 30 minutes at room temperature. The mixture was centrifuged and the pellet resuspended in 0.1 ml of SOS (1.2M sorbitol, 33% v/v YPD, 6.7 mM $CaCl_2$, 14 µg/ml leucine) and incubated at 30° C. for 2 hours. The suspension was then centrifuged and the pellet resuspended in 0.5 ml of 1.2M sorbitol. Then, 6 ml of top agar (the SC medium of Sherman et al., (Methods in Yeast Genetics, Cold Spring Harbor Laboratory, 1981) containing 1.2M sorbitol plus 2.5% agar) at 52° C. was added and the suspension poured on top of plates containing the same agar-solidified, sorbitol containing medium. Transformant colonies were picked after 3 days at 30° C., reisolated and used to start liquid cultures. One such transformant KFN-883 was selected for further characterization.

Yeast strain KFN-883 was grown on YPD medium (1% yeast extract, 2% peptone (from Difco Laboratories), and 2% glucose). A 10 ml culture of the strain was shaken at 30° C. to an O.D. at 600 nm of 20. After centrifugation the supernatant was analyzed by HPLC as described (Snel et al., *Chromatographia* 24 (1987), 329–332). The yield was about 0.14 mg/liter of insulin B(1–27)-Lys-Ala-Ala-Lys-A(1–20)-Ser.

The single chain insulin precursor was isolated from the fermentation supernatant by adsorption to an ion exchange column at low pH, desorption at high pH and precipitation of the pool by zinc ions. Transpeptidation of the precursor to $[Ser^{A21}],des[Pro^{B28}],[Thr^{B30}OMe]$ human insulin was as follows:

10 mmol (2.35 g) of threonine methylester and glacial acetic acid was dissolved in DMF to give 5 ml, 2.5 ml 76.5% v/v DMF in water was added and 0.5 g of precursor was dissolved in the mixture, which was kept at 12° C.; then 50 mg of trypsin in 1.25 ml 0.05M calcium acetate was added and after 24 hours at 12° C. the reaction mixture was added to 100 ml of acetone for precipitation of the peptides, which were spun down and dried in vacuo.

The isolated insulin analogue ester was purified on a preparative HPLC column using a silica-C18 matrix at acidic pH. Then the purified ester was hydrolyzed in aqueous medium at pH 10 and 25° C. for 24 hours. The $[Ser^{A21}],des[Pro^{B28}]$ human insulin formed was precipitated at neutral pH with zinc ions. The precipitate was purified by anion exchange chromatography and subsequently desalted by gel filtration. Yield of lyophilized $[Ser^{A21}],des[Pro^{B28}]$ human insulin was 102 mg.

EXAMPLE 13

Preparation of $des[Thr^{B27}]$ human insulin 1 g of Zn-free porcine insulin was dissolved in 40 ml of water by adjusting the pH value to 9, and a solution of 50 mg of porcine trypsin in 10 ml of 0.25M ammonium hydrogen carbonate adjusted to pH 9 with ammonia solution was added. The solution was then left at 4° C. and after 48 hours a yield of 65% was found by HPLC analysis. The reaction mixture was then gel filtrated at 4° C. on a 5×90 cm column of Sephadex® G50 superfine in 0.05M ammonium hydrogen carbonate with a flow of 90 ml per hour. Fractions containing the main protein peak were pooled and lyophilized. The yield was 520 mg of des(B23–B30) human insulin.

A peptide with the sequence Gly-Phe-Phe-Tyr-Pro-Lys-Thr was synthesized on a PAM resin by means of protected symmetrical amino acid anhydrides by means of a peptide synthesis apparatus from Applied Biosystems. Finally, the peptide was cleaved from the resin by anhydrous hydrogen fluoride at 0° C., whereby the remaining protecting groups were simultaneously removed.

200 mg of des(B23–B30) human insulin and 400 mg of peptide were dissolved in a mixture of 2.40 ml of dimethyl formamide and 1.20 ml of water and the pH value of the mixture was adjusted 6.5 with triethyl amine. 10 mg of porcine trypsin in 0.20 ml of water was then added and the reaction mixture was left at 20° C. for 4 hours. The reaction was then stopped by addition of 25 ml of 2-propanol and the precipitated proteins were isolated by centrifugation. The drained precipitate was redissolved in 10 ml of 1M acetic acid and applied to a 2.6×20 cm column of Lichroprep® RP-18 (25–40 µm) previously equilibrated with 0.5 mM hydrochloric acid, 0.1M sodium chloride in 30% (by volume) ethanol. The column was then eluted at 20° C. at a flow of 20 ml per hour with the same buffer but with a linear increase of the ethanol content to 50% over 24 hours. The eluate was monitored for UV-absorption and fractions containing the main protein peak were pooled. The protein was precipitated by dilution with the same volume of water and adjustment of the pH-value to 5.5 with sodium hydroxide solution, and after standing at 4° C. for 1 hour the precipitate was isolated by centrifugation and lyophilization.

The yield was 80 mg of $des[Thr^{B27}]$ human insulin, which was identified by sequential Edman degradation of the separated vinyl pyridylated A- and B-chains.

EXAMPLE 14

Formulation of injectable solution

60 µmoles of a human insulin analogue according to the invention were dissolved in 4 ml of 0.1M HCl and 20 ml of 1.5% m-cresol were added. The solution is now mixed with 40 ml of 4% glycerol and 20 ml of 65 mM disodium hydrogen phosphate, and the pH value was adjusted to 7.3. Finally the solution was adjusted to 100 ml with water and sterilized by filtration.

EXAMPLE 15

Evaluation of the degree of association

A 2.6 cm×88 cm column of Sephadex®G-75 was equilibrated with 13 mM sodium phosphate buffer pH 7.3 with a flow of 22 ml/hour. By application of des (octapeptide$^{B23-B30}$) human insulin, cytochrome C, ribonuclease and mono- and dimeric myoglobin as molecular weight markers a curve representing the molecular weight as a function of the elution volume was drawn.

By application of 1 ml of solution containing 0.6 mM Zn-free human insulin or 0.6 mM insulin analogue and prepared as described in example XII it was found that Zn-free human insulin elutes as a tailing peak with an apparent molecular weight of ≈14 kD and that the analogues prepared as described in the examples VI to X all were eluted as a symmetric peak with an apparent molecular weight of ≈5 kD.

These results indicate that human insulin analogues according to the invention are essential monomeric in solution at pH 7.3, whereas the normal human insulin under the same conditions to a high degree appears as a mixture of dimers and higher oligomers.

EXAMPLE 16

Evaluation of biological activity

The biological activity in vitro was determined by measuring the binding affinity to the insulin receptors of isolated rat adipocytes and hepatocytes essentially as described by Gliemann and Gammeltoft in *Diabetologia* 10 (1974), 105–113.

The insulin analogues were compared to semisynthetic human insulin, the potency of which was set to 100%, and the results are shown in the table below:

|  | Adipocytes | Hepatocytes |
|---|---|---|
| des[Phe$^{B25}$],des[Thr$^{B30}$] human insulin | 223% | 201% |
| des[Phe$^{B25}$]human insulin | 225% | 249% |
| [Asp$^{A21}$]-des[Phe$^{B25}$],des[Thr$^{B30}$] human insulin | 250% | 242% |

EXAMPLE 17

Demonstration of rapidly occurring biological effect after subcutaneous injection of des[Pro$^{B28}$],des[Thr$^{B30}$] human insulin in pigs An injectable solution containing 0.6 mM of des[Pro$^{B28}$] des[Thr$^{B30}$] human insulin was prepared in accordance with the method described in example 18.

In a cross-over experiment, 6 healthy pigs weighing 70–100 kg received subcutaneous injections of 1 μ/kg either of this preparation or of the commercially available rapid acting human insulin preparation Actrapid® (100 IU/ml, 0.6 mM) and blood samples were collected from the ear vein at intervals of 20–30 minutes for 5 hours. The glucose concentration was determined in the samples and the average value from the 6 pigs after each time interval was calculated. The difference between glucose concentration and the mean initial value was then depicted against the time as shown in FIG. 5.

Figure 5:
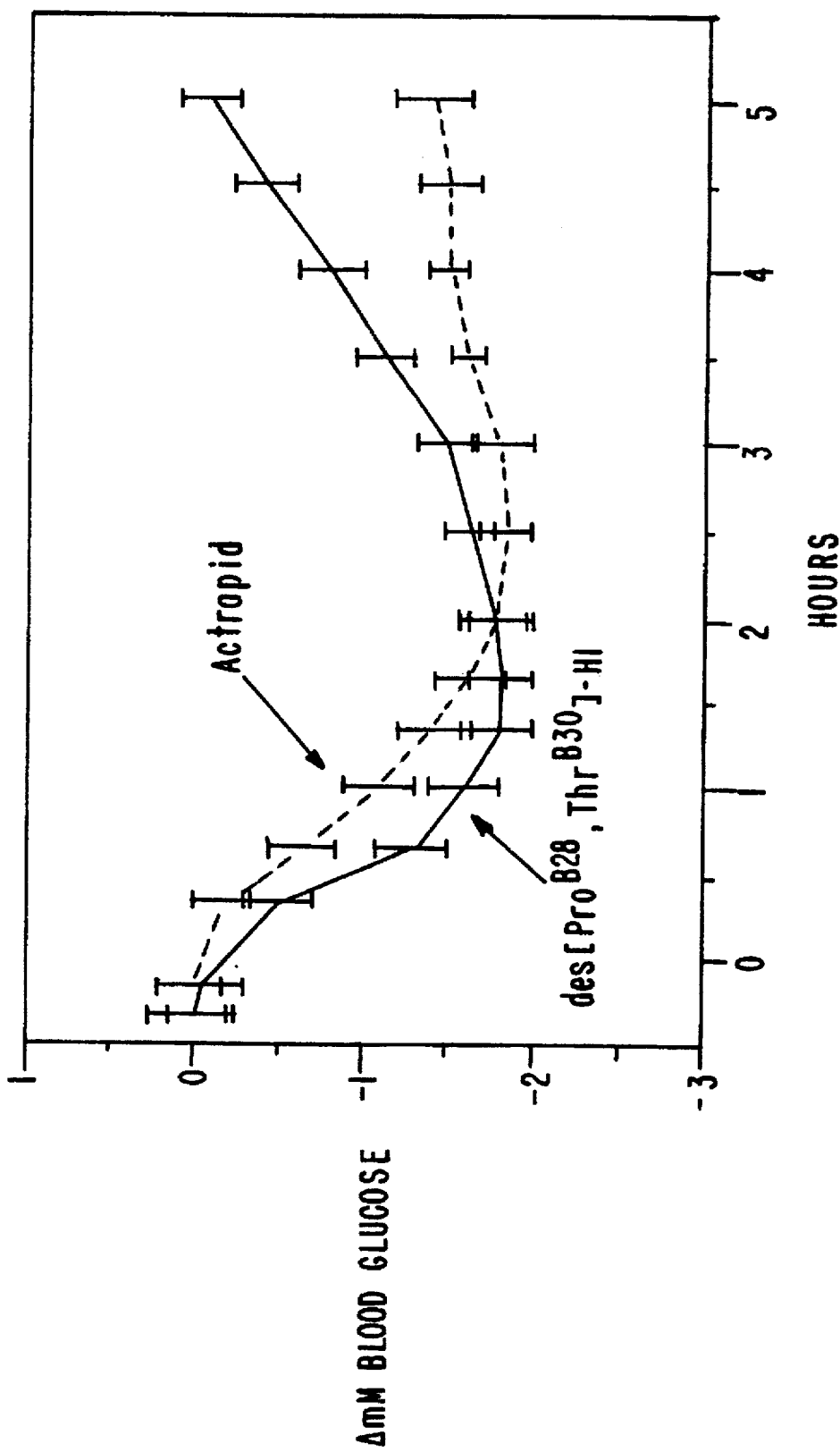
FIG. 5 shows the blood glucose effect of des[Pro$^{B28}$],des[Thr$^{B30}$] human insulin in pigs.

FIG. 5 illustrates that the preparation containing des [Pro$^{B28}$],des[Thr$^{B30}$] human insulin shows a substantially more rapid onset of the glucose-lowering effect than the conventional human insulin preparation Actrapid®. The maximum effect is achieved after 100 minutes versus 150 minutes for Actrapid®.

We claim:

1. An insulin analog which is des[Pro$^{B28}$], des[Thr$^{B30}$] human insulin or a pharmaceutically acceptable salt thereof.

2. A pharmaceutical composition comprising the insulin analog according to claim 1 and a pharmaceutically acceptable carrier or diluent.

3. The pharmaceutical composition according to claim 2, wherein the insulin analog is in monomeric form.

4. The pharmaceutical composition according to claim 2, wherein the pharmaceutical composition is formulated as an aqueous solution.

5. The pharmaceutical composition according to claim 2, wherein the pharmaceutical composition is formulated as an aqueous suspension.

6. The pharmaceutical composition according to claim 2, wherein the pharmaceutically acceptable carrier is an aqueous, isotonic solution.

7. The pharmaceutical composition according to claim 2, which further comprises zinc ions.

8. The pharmaceutical composition according to claim 2, which further comprises a buffer.

9. The pharmaceutical composition according to claim 8, wherein the buffer is acetate or citrate.

10. The pharmaceutical composition according to claim 2, which further comprises a preservative.

11. The pharmaceutical composition according to claim 10, wherein the preservative is m-cresol, methylparaben or phenol.

12. A method of treating diabetes mellitus comprising administering to an effected individual the pharmaceutical composition according to claim 2.

13. An insulin analog selected from the group consisting of des[Pro$^{B28}$] human insulin, des[Phe$^{B25}$] porcine insulin, des[Pro$^{B28}$] porcine insulin, des[Pro$^{B28}$] rabbit insulin, des[Phe$^{B25}$], des[Thr$^{B30}$] human insulin, des[Tyr$^{B26}$], des[Thr$^{B30}$] human insulin,

[Ser$^{A21}$]-des[Pro$^{B28}$] human insulin,

[Gly$^{A21}$]-des[Pro$^{B28}$] human insulin,

[Gly$^{A21}$]-des[Phe$^{B25}$] human insulin,

[Asp$^{A21}$]-des[Phe$^{B25}$] human insulin,

[His$^{B25}$]-des[Tyr$^{B26}$], des[Thr$^{B30}$] human insulin,

[Asn$^{B25}$]-des[Tyr$^{B26}$], des[Thr$^{B30}$] human insulin,

[Asp$^{A21}$]-des[Phe$^{B25}$], des[Thr$^{B30}$] human insulin,

[Asp$^{B28}$]-des[Phe$^{B25}$] human insulin,

[Asp$^{B3}$]-des[Phe$^{B25}$] human insulin,

[Lys$^{B28}$, Thr$^{B29}$] human insulin,

[Arg$^{B28}$]-des[Lys$^{B29}$] human insulin,

[Gly$^{A21}$]-des[Thr$^{B27}$] human insulin,

[Gly$^{A21}$, Thr$^{B3}$]-des[Thr$^{B27}$] human insulin,

[Ala$^{A21}$, Thr$^{B3}$]-des[Thr$^{B27}$] human insulin,

[Gly$^{A21}$, Asp$^{B3}$]-des[Thr$^{B27}$] human insulin,
[Ala$^{A21}$, Asp$^{B3}$]-des[Thr$^{B27}$] human insulin,
des[Thr$^{B27}$], des[Thr$^{B30}$] human insulin, and pharmaceutically acceptable salts thereof.

14. A human insulin analog having a deletion of the amino acid at one of the positions B24, B25, B26, B27 or B28 and having a deletion of the amino acid at one or both of B29 and B30, or a pharmaceutically acceptable salt thereof.

15. A human insulin analog having Arg substituted for Pro at position B28, or a pharmaceutically acceptable salt thereof.

16. A human insulin analog having Arg or Lys substituted for Pro at position B28 and having a deletion of the amino acid at one or both of B29 and B30, or a pharmaceutically acceptable salt thereof.

17. A human insulin analog having a deletion of the amino acid at one of the positions B24, B25, B26, B27 or B28 and having Arg substituted for Lys at position B29, or a pharmaceutically acceptable salt thereof.

* * * * *

UNITED STATES PATENT AND TRADEMARK OFFICE
CERTIFICATE OF CORRECTION

PATENT NO. : 5,716,927
DATED : February 10, 1998
INVENTOR(S) : Balschmidt et al

It is certified that error appears in the above-identified patent and that said Letters Patent is hereby corrected as shown below:

On the title page: Item [75] Inventors: please delete "Esperdaede" and insert "Espergaerde".

[*] Notice: please delete "5,164,364" and insert "5,164,366"

Item [56] under "Attorney, Agent, or Firm" please delete "Elies" and insert "Elias"

Col. 2, line 4: delete "And" and insert "and"
Col. 2, line 27: delete "analoguss" and insert "analogues"
Col. 6. line 57: delete "analoguss" and insert "analogues"
Col. 7, line 2: delete "analoguss" and insert "analogous"
Col. 7, line 44: delete "analoguss" and insert "analogous"
Col. 7, line 64: delete "synthetia" and insert "synthetic"
Col. 7, line 65: delete "analoguss" and insert "analogues"
Col. 7, line 65: delete "maybe" and insert "may be"
Col. 8, line 12: delete "analoguss" and insert "analogues"

UNITED STATES PATENT AND TRADEMARK OFFICE
CERTIFICATE OF CORRECTION

PATENT NO. : 5,716,927
DATED : February 10, 1998
INVENTOR(S) : Balschmidt et al.

It is certified that error appears in the above-identified patent and that said Letters Patent is hereby corrected as shown below:

Col. 8, line 13: delete "analoguss" and insert "analogues"
Col. 9, line 47: delete "phosphorylatipn" and insert "phosphorylation"
Col. 9, line 52: delete "ImM" and insert 1mM"
Col. 14, line 58: delete "frame" after "in-frame"
Col. 14, line 65: delete "=XbaI" and insert "-XbaI"
Col. 15, line 5: delete "pHT636" and insert "pMT636"
Col. 16, line 42: insert "to" after "adjusted"
Col. 17, line 26: delete "essential" and insert "essentially"

Signed and Sealed this

Eighth Day of December, 1998

Attest:

BRUCE LEHMAN

*Attesting Officer*    *Commissioner of Patents and Trademarks*